United States Patent
Wang et al.

(10) Patent No.: US 12,053,822 B2
(45) Date of Patent: Aug. 6, 2024

(54) SYSTEM AND METHOD FOR MITIGATING METAL PARTICLE LEAKAGE FROM ADDITIVE THREE-DIMENSIONAL PRINTED PARTS

(71) Applicant: GE PRECISION HEALTHCARE LLC, Wauwatosa, WI (US)

(72) Inventors: Yanju Wang, Hartland, WI (US); Jaroslaw Kurzac, Oconomowoc, WI (US); Chad Allan Smith, Franklin, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 89 days.

(21) Appl. No.: 17/141,773

(22) Filed: Jan. 5, 2021

(65) Prior Publication Data

US 2022/0212260 A1 Jul. 7, 2022

(51) Int. Cl.
| | | |
|---|---|---|
| *B22F 10/60* | (2021.01) | |
| *B22F 10/68* | (2021.01) | |
| *B33Y 40/20* | (2020.01) | |
| *B33Y 80/00* | (2015.01) | |
| *G21K 1/02* | (2006.01) | |
| *A61B 6/03* | (2006.01) | |
| *A61B 6/10* | (2006.01) | |

(52) U.S. Cl.
CPC .............. *B22F 10/60* (2021.01); *B22F 10/68* (2021.01); *B33Y 40/20* (2020.01); *B33Y 80/00* (2014.12); *G21K 1/02* (2013.01); *A61B 6/032* (2013.01); *A61B 6/107* (2013.01); *B22F 2301/20* (2013.01)

(58) Field of Classification Search
CPC .......... B22F 10/10; B22F 10/14; B22F 10/16; B22F 10/20; B22F 10/25; B22F 10/28; B22F 10/60; B22F 10/62; B22F 10/66; B33Y 10/00; B33Y 40/20
See application file for complete search history.

(56) References Cited

U.S. PATENT DOCUMENTS

| | | | | |
|---|---|---|---|---|
| 5,749,041 A | * | 5/1998 | Lakshminarayan | .... B22F 10/20 419/29 |
| 7,627,089 B2 | * | 12/2009 | Rantanen | ................. G21K 1/02 378/147 |
| 9,943,981 B2 | * | 4/2018 | Günther | .............. C04B 41/4545 |

(Continued)

FOREIGN PATENT DOCUMENTS

| | | |
|---|---|---|
| CN | 103660654 A | 3/2014 |
| JP | 5893292 A | 6/1983 |
| JP | 2018188727 A | 11/2018 |

OTHER PUBLICATIONS

Gaget, Lucie; "Conductive 3D Printing: How can additive manufacturing help electronics?", Sep. 4, 2018, pp. 1-5; https://www.sculpteo.com/blog/2018/09/04/conductive-3d-printing-how-can-additive-manufacturing-help-electronics/.

(Continued)

*Primary Examiner* — Michael P Wieczorek

(57) ABSTRACT

A method is provided for mitigating metal particle leakage from a three-dimensional printed part. The method includes providing an additively manufactured part manufactured out of one or more materials, and the one or more materials comprise a metal. The method also includes applying a coating over surfaces of the additively manufactured part to keep metal particles from leaking from the additively manufactured part.

17 Claims, 2 Drawing Sheets

(56) References Cited

U.S. PATENT DOCUMENTS 10,174,414 B2    1/2019   Lin
10,322,454 B2 *  6/2019   Guo ........................ B22F 12/49

OTHER PUBLICATIONS

Benwood, Claire, et al.; "Improving the Impact Strength and Heat Resistance of 3D Printed Models: Structure, Property, and Processing Correlationships during Fused Deposition Modeling (FDM) of Poly(Lactic Acid)"; ACS Omega, 2018, pp. 4400-4411; https://pubs.acs.org/doi/10.1021/acsomega.8b00129.

U.S. Appl. No. 16/708,868, filed Dec. 10, 2019, Yanju Wang.

JP patent application 2021-202122 filed Dec. 14, 2021—Office Action issued Jan. 25, 2023, Machine Translation Jan. 26, 2023; 8 pages.

JPS58093292 Abstract—English Translation, Espacenet.com, Mar. 17, 2023; 1 page.

\* cited by examiner

SYSTEM AND METHOD FOR MITIGATING METAL PARTICLE LEAKAGE FROM ADDITIVE THREE-DIMENSIONAL PRINTED PARTS

BACKGROUND

The subject matter disclosed herein relates to imaging systems, and more particularly, to mitigating metal particle leakage from additive three-dimensional (3D) printed parts of the imaging systems.

Some components of an imaging system (e.g., computed tomography (CT) imaging system) may be printed or additively manufactured out of one or more materials. Some of these materials may include metal (e.g., metal powder). Loose or weakly attached powder particles (e.g., metal powder particles) may leach out from the 3D printed parts due to the nature of the additive manufacturing process. These leached out metal particles may cause image defects or the malfunction of other imaging components due to the rotating nature of a CT scanner. Typical cleaning techniques (e.g., air blowing, solvent or water rinse, ultrasound cleaning, etc.) may not be effective at completely removing these loose particles even if the cleaning is extensive (or in some cases may further promote this leakage). For example, an imaging system may include one or more collimator modules (e.g., additively manufactured collimator modules). The collimator modules may be utilized under a wide range of loads (e.g., in a high speed spin or slow rotation) and subjected to vibrations (e.g., from scanners) that cause loose particles to move around that can impact clinical images (e.g., due to density of the particles) or cause damage to other imaging components (e.g., by entering within precision ceramic bearings).

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one implementation, a method is provided for mitigating metal particle leakage from a three-dimensional printed part. The method includes providing an additively manufactured part manufactured out of one or more materials, and the one or more materials comprise a metal. The method also includes applying a coating over surfaces of the additively manufactured part to keep metal particles from leaking from the additively manufactured part.

In a further implementation, a method is provided for mitigating metal particle leakage from a three-dimensional printed collimator. The method includes providing an additively manufactured collimator manufactured out of one or more materials, the one or more materials comprise a metal, and the additively manufactured collimator is configured to provide collimation on a beam emitted from an X-ray source of an imaging system. The method also includes applying a coating over surfaces of the additively manufactured collimator to keep metal particles from leaking from the additively manufactured collimator.

In an additional implementation, an imaging system is provided. The imaging system includes an additively manufactured three-dimensional (3D) collimator manufactured out of one or more materials, the one or more materials comprise a metal, and the additively manufactured (3D) collimator is configured to provide collimation on a beam emitted from an X-ray source of the imaging system. The imaging system also includes a coating disposed over surfaces of the additively manufactured 3D collimator, wherein the coating is configured to keep metal particles from leaking from the additively manufactured 3D collimator.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Figure 1:
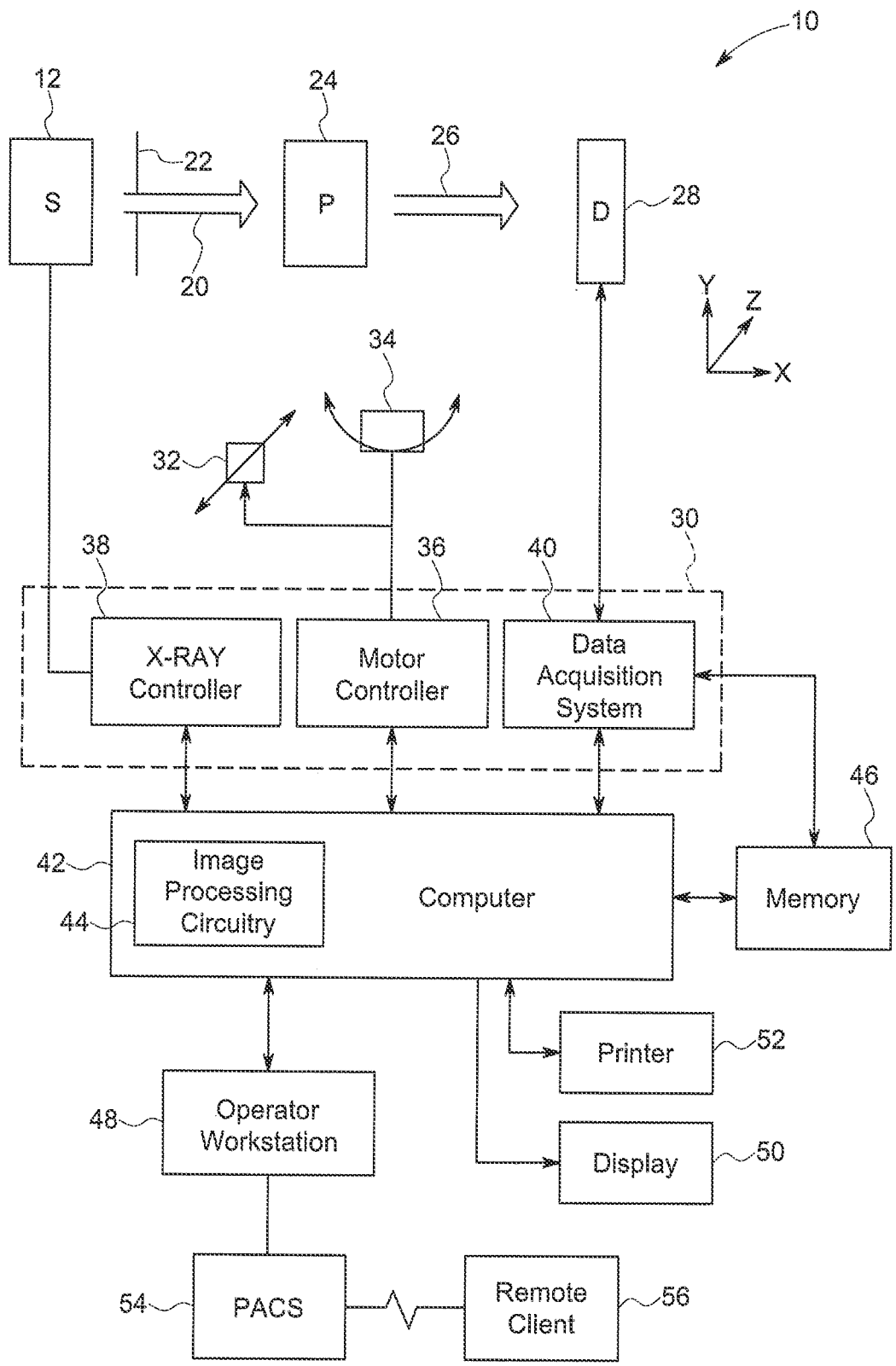
FIG. 1 is a block diagram representation of a CT system, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as imaging (e.g., in industrial use) in non-destructive inspection of manufactured parts or goods (i.e., quality control or quality review applications), and/or the non-invasive inspection of packages, boxes, luggage, and so forth (i.e., security or screening applications). Further, the present approaches may be utilized in any application where it may be beneficial to avoid the leaking of metal particles from an additively manufactured part. In general, the present approaches may be useful in any context where additive manufacturing is utilized.

The present disclosure provides for systems and methods for mitigating metal particle leakage from three-dimensional (3D) printed or additively manufactured parts (e.g., of an imaging system). In particular, a coating is applied to the printed part to avoid the leakage of metal particles. In the context of medical imaging, avoiding the leakage of metal particles from the printed part may avoid image defects and/or the malfunction of other imaging components. In certain embodiments, the coating may be fine-tuned (e.g., include one or more materials) to improve or alter a characteristic or function of the printed part (e.g., mechanical strength, thermal conductivity, surface finish, etc.). The coating may mitigate the need for extensive cleaning, thus, reducing the time to finish manufacturing the printed part, while avoiding both producing particle residues and damage to the printed part.

With the foregoing discussion in mind, FIG. 1 illustrates an embodiment of an imaging system 10 for acquiring and processing image data that may utilize 3D additively manufactured or printed parts in accordance with aspects of the present disclosure. Although the following embodiments are discussed in terms of the computed tomography (CT) imaging system, the embodiments may also be utilized with other imaging systems (e.g., X-ray, PET, CT/PET, SPECT, nuclear CT, etc.). In the illustrated embodiment, system 10 is a computed tomography (CT) system designed to acquire X-ray projection data, to reconstruct the projection data into a tomographic image, and to process the image data for display and analysis. The CT imaging system 10 includes one or more X-ray sources 12, such as one or more X-ray tubes or solid-state emission structures which allow X-ray generation at one or more locations and/or one or more energy spectra during an imaging session.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements. Each detector element produces an electrical signal that represents the intensity of the X-ray beam incident at the position of the detector element when the beam strikes the detector 28. Electrical signals are acquired and processed to generate one or more scan datasets.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. In addition, in some embodiments the X-ray controller 38 may be configured to selectively activate the source 12 such that tubes or emitters at different locations within the system 10 may be operated in synchrony with one another or independent of one another.

The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer may include processing circuitry 44 (e.g., image processing circuitry). The computer 42 may include or communicate with one or more non-transitory memory devices 46 that can store data processed by the computer 42, data to be processed by the computer 42, or instructions to be executed by a processor (e.g., processing circuitry 44) of the computer 42. For example, the processing circuitry 44 of the computer 42 may execute one or more sets of instructions stored on the memory 46, which may be a memory of the computer 42, a memory of the processor, firmware, or a similar instantiation.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2:
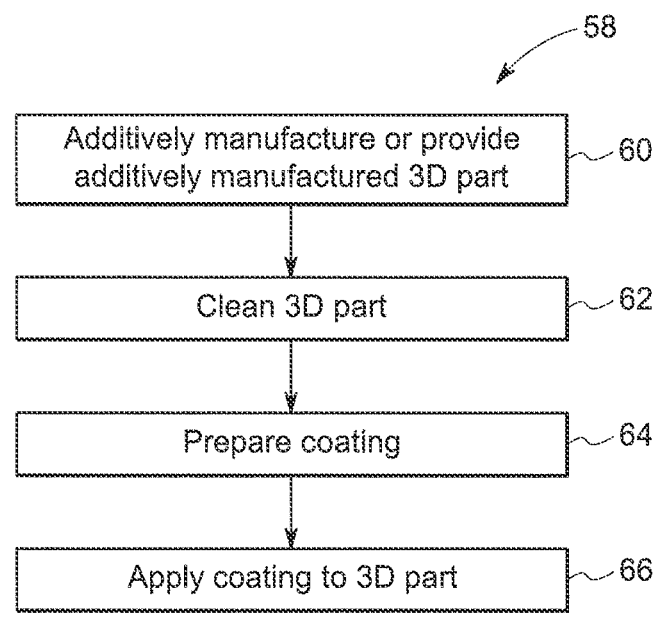
FIG. 2 is a flow chart for an embodiment of a method for producing a coated 3D printed part, in accordance with aspects of the present disclosure.

FIG. 2 is a flow chart for an embodiment of a method 58 for producing a coated 3D printed part. The method 58 includes additively manufacturing or providing an additively manufacturing 3D printed part (block 60). The printed part may be made of one or more materials. These materials may include one or more different metals (e.g., metal powders) depending on the part. In certain embodiments, the parts may be components of an imaging system (e.g., imaging system 10). For example, the parts may be a frame, circuitry, a collimator, or any other component that can be additively manufactured. The printed part may be additively manufactured via any additive manufacturing technique (e.g., laser powder bed fusion, photopolymerization, material jetting, binder jetting, material extrusion, sheet lamination, direct energy deposition, etc.).

The method 58 also includes cleaning the printed part (block 62). Typically, in the absence of a coating, printed parts undergo extensive cleaning repeatedly that is both time consuming and leaves particle residues (even after multiple days of cleaning). In addition, the extensive cleaning may physically damage the printed part. Extensive cleaning may include compressed air cleaning and blowing, solvent- or water-based cleaning, ultrasonic cleaning, or the addition of filtration units. With the coating, less cleaning of the printed parts may be needed compared to printed parts without the coating. For example, passive cleaning may be utilized before the application of the coating. Passive cleaning may include mechanical vibration or de-powdering.

The method 58 also includes preparing a coating (block 64). Preparing the coating may be as simple as getting it ready (e.g., mixing, if needed) for application depending of the composition of the coating. For example, the coating may include a mixture of materials. The coating may made of organic polymers or polymer composites. In certain embodiments, the coating may be made of non-reactive polymers, 1-part reactive polymers, or 2-part reactive polymers. In certain embodiments, the coating may be made of thermosetting polymers or thermoplastic polymers. In certain embodiments, the coating may be made of one or more of epoxies, polyurethanes, polyacrylics, cyanoacrylates, silicones, polyolefins, polyvinyl alcohol, rubbers, polyvinyl chloride, phenol formaldehyde, nylon, and polyacrylonitrile. In certain embodiments, the coating may be made of pure polymers or polymer blends. In certain embodiments, the coating may be made of a polymer composite that may include inorganic fillers, ceramic precursors, or fine metal particles. In certain embodiments, the coating may be fined tuned (e.g., include one or more materials) to improve or alter a characteristic or function of the printed part (e.g., mechanical strength, thermal conductivity, surface finish, etc.) depending on the application. For example, the coating may include a heavy metal powder (e.g., tungsten) configured to increase radiation shielding.

The method 58 further includes applying the coating to the printed part (block 66). For example, applying the coating may include immersing the printed part within the coating, spraying the coating on the printed part, brush coating the coating, or another technique. In certain embodiments, a coating with monomers or oligomers with cross-linkers may be coated to the surfaces of the printed part and then chemical crosslinking performed. In certain embodiments, the surfaces of the printed part may be coated with a polymer solution and then the polymer solution may be solidified via evaporation or cooling down of melted polymers. Typically, the coating may be a liquid that penetrates through the surfaces of the printed part to anywhere that the metal particles have the potential to leak out to and prevent the movement of the particles after curing or solidification. The coating may be applied separately to individual printed parts or applied to multiple printed parts at the same time.

Figure 3:
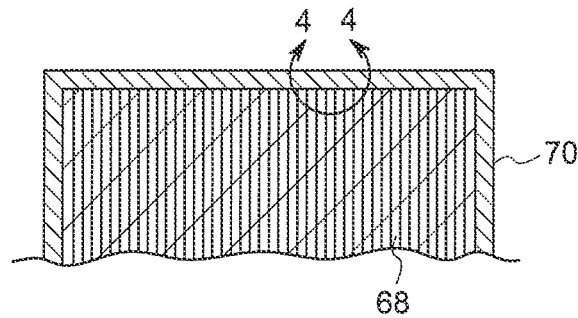
FIG. 3 is a schematic cross-sectional view of an embodiment of a portion of a coated 3D printed part (e.g., coated collimator), in accordance with aspects of the present disclosure.

FIG. 3 is a schematic cross-sectional view of a portion of a coated 3D printed part. As depicted, FIG. 3 includes a 3D printed part 68 and a coating 70 disposed over the surfaces of the 3D printed part 68. As noted above, the 3D printed part 68 may be any type of printed part that includes metal particles. For example, the printed part 68 may be a component of an imaging system (e.g., imaging system 10). For example, the printed part 68 may be a frame, electronics, collimator, or other component of the imaging system. As depicted in FIG. 3, the printed part 68 is a two-dimensional (2D) collimator. In the case of the coating 70 for the collimator, the coating 70 is almost transparent to radiation (i.e., the coating does not affect the functionality of the collimator with regard to collimation. A thickness of the coating 70 (e.g., of a few micrometers) is such that it does not influence the geometry of the printed part 68 nor cause the printed part 68 to exceed its engineering tolerance.

Figure 4:
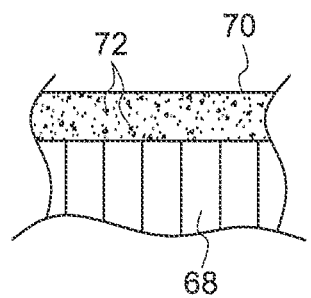
FIG. 4 is a cross-sectional view of the coated 3D printed part of FIG. 3, taken within line 4-4, in accordance with aspects of the present disclosure.

As mentioned above, the coating 70 may be fine-tuned (e.g., include one or more materials) to improve or alter a characteristic or function of the printed part 68 (e.g., mechanical strength, thermal conductivity, surface finish, etc.) depending on the application. FIG. 4 is a cross-sectional view of the coated 3d printed part 68 of FIG. 3, taken within line 4-4. As depicted, the coating 70 includes inorganic fillers, ceramic precursors, or fine metal particles 72. In certain embodiments, the coating 70 includes a heavy metal powder (e.g., tungsten) to increase radiation shielding when the printed part 68 is a collimator as in FIGS. 3 and 4.

Certain printed parts, such as a collimator are very fragile due to most walls being very thin (e.g., between approximately 30 micrometers and 300 micrometers). In the case of collimator, it is subject to a wide range of loads (e.g., from a high-speed spin to a slow rotation) that (in the absence of a coating) cause loose metal particles to leak from the collimator. The addition of the coating 70 to the collimator increases the collimator's mechanical strength and toughness. For example, a printed tungsten tensile bar (e.g., having the dimensions of approximately 250 millimeters (mm) for the length, 23.7 mm for the width, and 1.82 mm for the thickness) under a tensile strength test may have a maximum load (N) of 2753. However, the same bar coated in a first epoxy-based coating and a second epoxy-based coating has maximum loads of 3613 and 2954, respectively. Thus, the coating increases the mechanical strength of the printed part (such as a collimator).

As discussed herein, technical effects of the disclosed subject matter include providing a coating on an additively manufactured or printed 3D part (e.g., imaging system component such as a collimator). The coating applied to the printed part minimizes or avoids the leakage of metal particles from the printed part. In the context of medical imaging, avoiding the leakage of metal particles from the printed part may avoid image defects and/or the malfunction of other imaging components. In certain embodiments, the coating may be fine-tuned (e.g., include one or more materials) to improve or alter a characteristic or function of the printed part (e.g., mechanical strength, thermal conductivity, surface finish, etc.). The coating may mitigate the need for extensive cleaning, thus, reducing the time to finish manufacturing the printed part and avoiding both producing particle residues and damage to the printed part during the cleaning.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for mitigating particle leakage from an additively manufactured part, comprising:
producing the additively manufactured part from a heavy metal powder;
applying a coating over external surfaces of the additively manufactured part to prevent particles from leaking from the additively manufactured part, wherein the coating comprises a polymer composite with inorganic fillers, ceramic precursors, or fine metal particles;
wherein the heavy metal powder and the additively manufactured part comprises tungsten;
wherein the tungsten increases X-ray radiation shielding of the additively manufactured part.

2. The method of claim 1, wherein the additively manufactured part comprises a component of an imaging system.

3. The method of claim 2, wherein the additively manufactured part comprises a collimator.

4. The method of claim 2, wherein the imaging system comprises a computed tomography imaging system.

5. The method of claim 1, wherein the coating comprises a two-part reactive polymer, a one-part reactive polymer, or a non-reactive polymer.

6. The method of claim 1, wherein applying the coating comprises coating external surfaces of the additively manufactured part with a coating having monomers or oligomers with crosslinkers on the additively manufactured part and performing chemical crosslinking.

7. The method of claim 1, wherein applying the coating comprises coating external surfaces of the additively manufactured part with a coating having a polymer solution on the additively manufactured part and solidifying the polymer solution via evaporation or cooling down of melted polymers.

8. The method of claim 1, wherein the coating comprises thermosetting polymers or thermoplastic polymers.

9. The method of claim 8, wherein the coating comprises one or more of epoxies, polyurethanes, polyacrylics, cyanoacrylates, silicones, polyolefins, polyvinyl alcohol, rubbers, polyvinyl chloride, phenol formaldehyde, nylon, and polyacrylonitrile.

10. The method of claim 1, wherein the coating comprises pure polymers or polymer blends.

11. The method of claim 1, further comprising cleaning the additively manufactured part that is to be coated, wherein the cleaning comprises mechanically vibrating or de-powdering the additively manufactured part.

12. The method of claim 1, wherein the coating is configured to increase a mechanical strength of the additively manufactured part compared to the additively manufactured part without the coating.

13. The method of claim 1, wherein applying the coating includes spraying the coating on the additively manufactured part.

14. The method of claim 1, wherein applying the coating includes brushing the coating on the additively manufactured part.

15. The method of claim 1, wherein applying the coating includes immersing the additively manufactured part in the coating.

16. A method for mitigating particle leakage from a three-dimensional printed collimator, comprising:
producing the three-dimensional printed collimator from a heavy metal powder, the three-dimensional printed collimator is configured to provide collimation of an X-ray beam emitted from an X-ray source of an imaging system; and
applying a coating over external surfaces of the additively manufactured collimator to prevent particles from leaking from the three-dimensional printed collimator, wherein the coating comprises a polymer composite with inorganic fillers, ceramic precursors, or fine metal particles;
wherein the heavy metal powder and the three-dimensional printed collimator comprises tungsten;
wherein the tungsten increases X-ray radiation shielding of the three-dimensional printed collimator.

17. The method of claim 16, wherein the imaging system comprises a computed tomography imaging system.

* * * * *